United States Patent [19]

Laborit et al.

[11] Patent Number: 5,391,761
[45] Date of Patent: Feb. 21, 1995

[54] PREPARATION OF NOVEL AMIDO-ALCOHOL DERIVATIVES AND THEIR THERAPEUTIC USES

[75] Inventors: Henri Laborit, Paris; Robert Zerbib, Issy-Les-Moulineaux; Philippe Dostert, Paris, all of France

[73] Assignee: Centre D'etudes Experimentals et Cliniques de Pharmacologie et D'Eutonologie (CEPBEPE), France

[21] Appl. No.: 89,114

[22] Filed: Jul. 8, 1993

[30] Foreign Application Priority Data

Jul. 8, 1992 [FR] France .................. 92 08462

[51] Int. Cl.⁶ .............. A61K 31/40; A61K 31/47; A61K 31/55; C07D 217/00; C07D 487/08; C07D 209/02

[52] U.S. Cl. ................... 548/452; 546/142; 540/576

[58] Field of Search .......... 548/452; 540/576; 546/146; 514/213, 308, 359

[56] References Cited

PUBLICATIONS

M. Kiyoshi et al, Chem. Abst., 112, (1990), 679; 178042J.

D. C. H. Bigg et al, Synthesis, No. 3, Mar., 1992, 277-278.

*Primary Examiner*—David B. Springer
*Attorney, Agent, or Firm*—Rosenman & Colin

[57] ABSTRACT

Cyclic amido alcohols of formula I are useful in the treatment of neurological and psychiatric disorders.

6 Claims, 10 Drawing Sheets

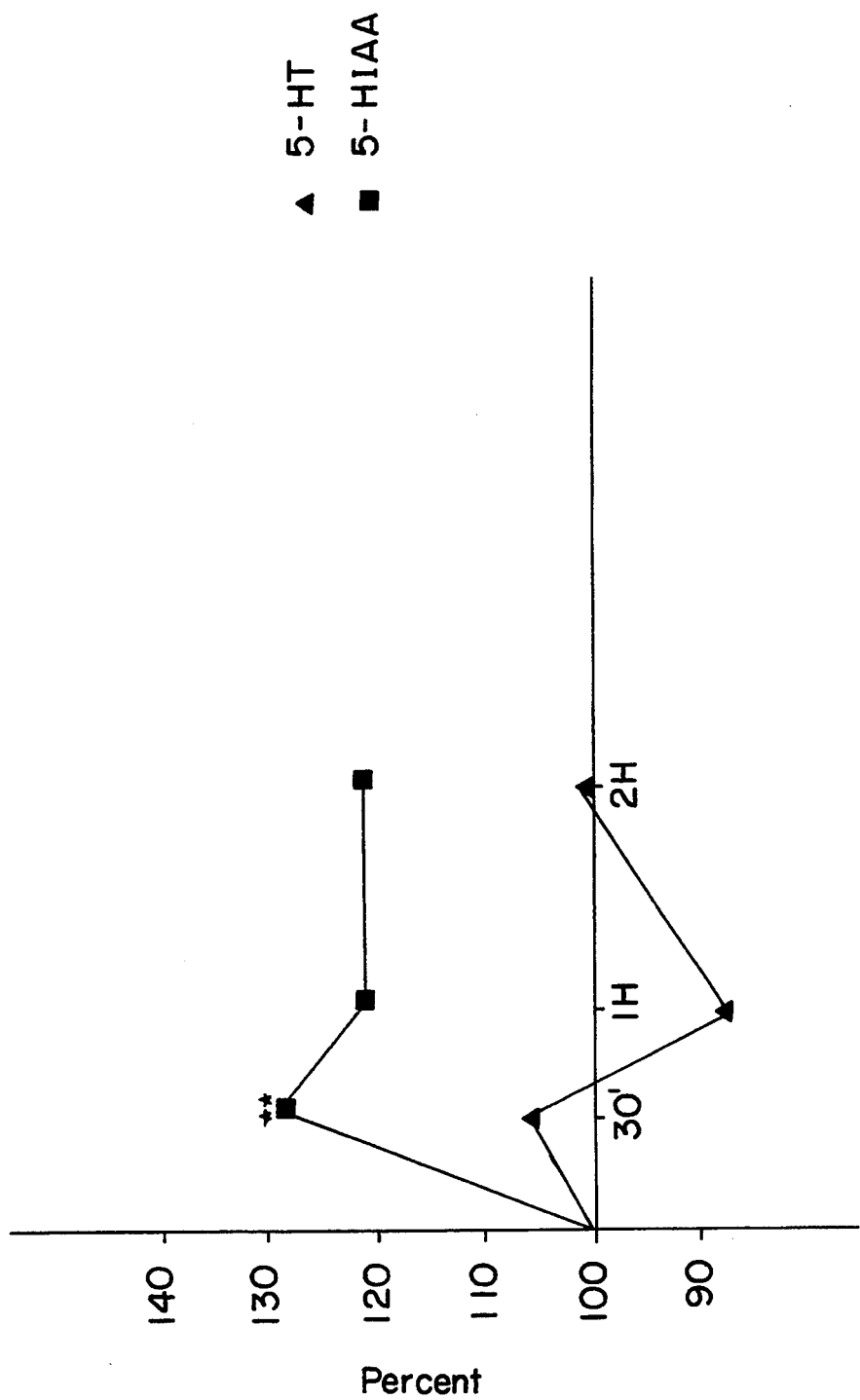

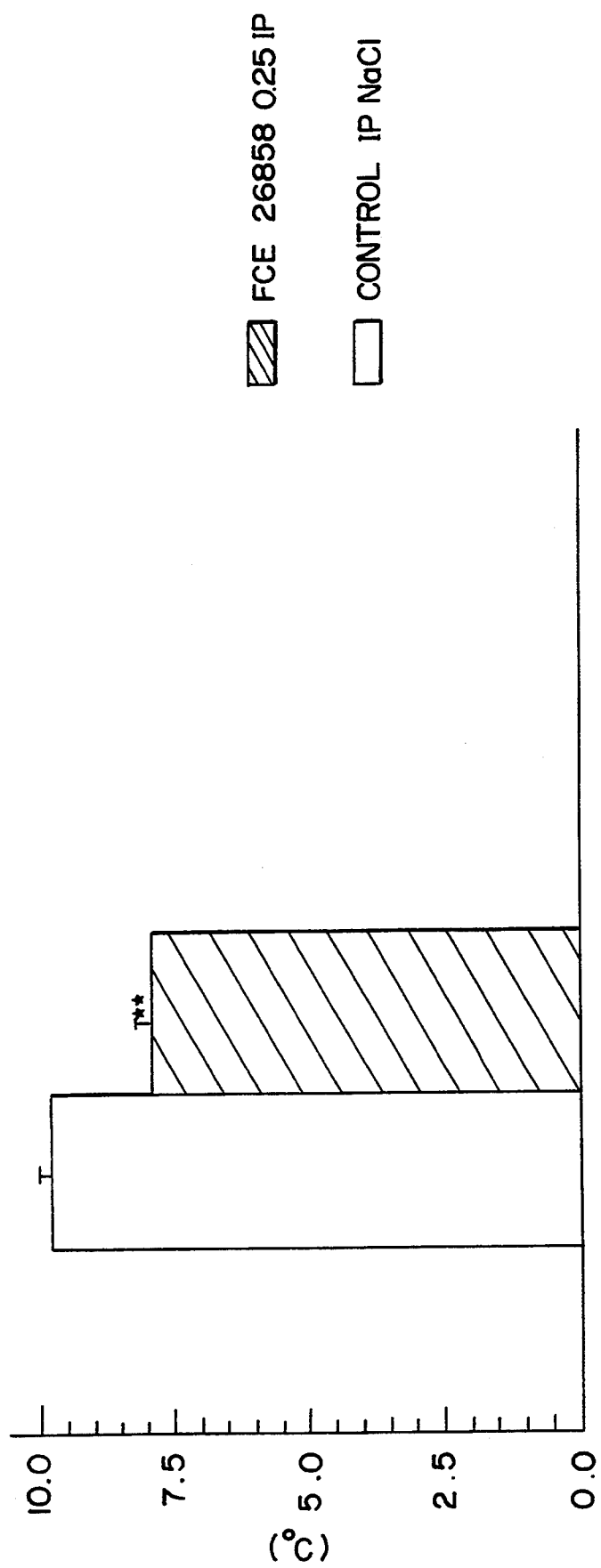

PREPARATION OF NOVEL AMIDO-ALCOHOL DERIVATIVES AND THEIR THERAPEUTIC USES

The present invention relates to a new family of chemical compounds the members of which are distinguished by their psychotropic action.

They are represented by the general formula (I)

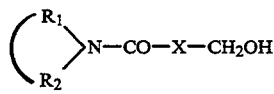

in which the cyclic system

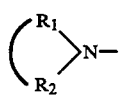

represents piperidine, nor-tropane, 3-aza-bicyclo[3,2,2-]nonane,6-azabicyclo[3,2,1]octane or tetrahydro-1,2,3,4-isoquinoline, possibly substituted by one or more alkyl groups and X represents the radical $CH_2$—$CH_2$ or CH=CH (trans).

The structure of some of these compounds is indicated in Table 1 and described in the specification.

The compounds of the invention are obtained by two different methods, depending on whether:

a)—X is $CH_2$—$CH_2$ in which case the compounds I are obtained by reaction of an amine

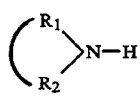

(A) with γ-butyrolactone by refluxing in a solvent such as benzene or toluene

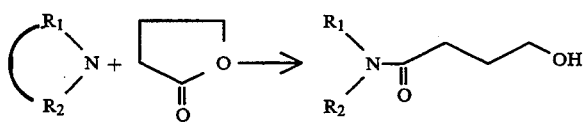

The compound in accordance with the invention in which

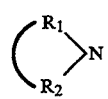

is the piperidine cycle had been previously obtained (Bull. Chem. soc. Jpn. 62:3138–3142, 1989) by reaction of the piperidine with the γ-butyrolactone under high pressure. To the best of our knowledge, the other compounds are new.

b)—X is CH=CH (trans)

In this case the compounds I are obtained by reduction of the acid II. First of all, II is reacted with a chloroformate, such as ethyl chloroformate, in the presence of a proton acceptor such as triethylamine (TEA), whereupon the reduction is effected by the addition of sodium borohydride:

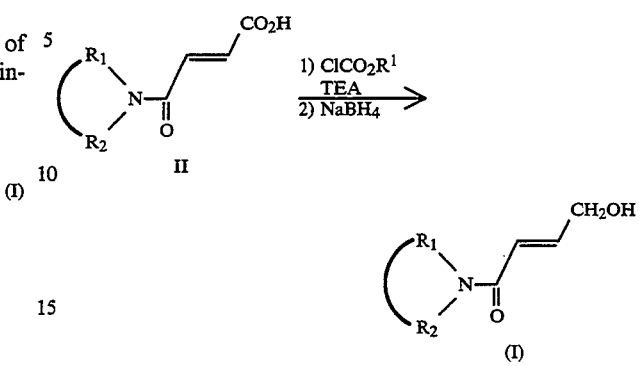

The acid II is obtained by basic hydrolysis by methanolic caustic potash or soda of the corresponding ester III, in which $R_3$ represents an alkyl group, preferably an ethyl group, in accordance with the equation:

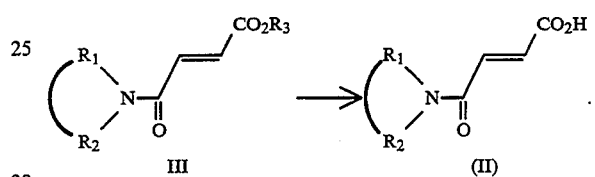

The ester III is obtained by reaction of an amine A with the semichloride of a semiester of fumaric acid IV, obtained in accordance with J. Chem. Soc., p. 1501 (1951), in which the $R_3$ group has the same meaning as previously, in the presence of a proton acceptor such as triethylamine:

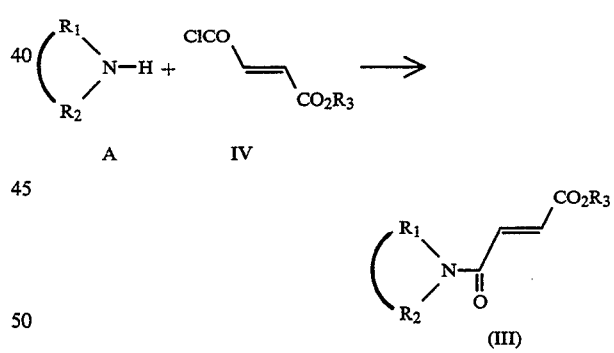

The synthesis of the following compounds is given by way of example:

Example 1 compounds with A=$CH_2$=$CH_2$

N-(γ-hydroxybutyryl)piperidine (FCE 26099)

The solution of 8.6 g (0.1 mol) of γ-butyrolactone and 12.8 g (0.15 mol) of piperidine in 75 ml of anhydrous benzene is refluxed for 5 hours. The solution is evaporated to dryness under vacuum and the residue is purified over a silica column by flash chromatography using a 90:10:1 mixture of $CHCl_3$/MeOH/$NH_4OH$ (30%) as eluant.

In this way there are obtained 13.5 g of N-(γ-hydroxybutyryl)piperidine (yield: 78.9%), melting point:

31°-33° C.; the literature (Bull. Chem. Soc. Jpn. 62:3138-3142, 1989) describes this product as an oil.

In similar manner there were obtained:
from nortropane, the derivative:

N- (γ-hydroxybutyryl)nortropane (FCE 26630); yield 57%; $n_D^{20}$=1.5164; NMR, (CDCl$_3$: 1.4–2.0 (12H, m), 2.3–2.6 (2H, m, CO—CH$_2$). 3.65 (2H, t, CH$_2$OH), 4.12 (1H, m), 4.62 (1H, m).

from 3-azabicyclo[3,2,2]nonane, the derivative:

3- (γ-hydroxybutyryl) -3-azabicyclo[3,2,2]nonane (FCE 26857); yield 74.8%, $n_D^{20}$=1.5240; NMR, (CDCl$_3$): 1.5–2.1 (12H, m), 2.5 (2H, t, COCH$_2$), 3.21 (1H, t, OH), 3.55 (2H, d, NCH$_2$), 3.65 (2H, t, CH$_2$OH), 3.70 (2H, d, N—CH$_2$).

from 1,3,3-trimethyl-6-azabicyclo[3,2,1]octane, the derivative:

6-(γ-hydroxybutyryl)-1,3,3-trimethyl-6-azabicyclo[3,2,1]octane (FCE 26858); yield 78.3% , $n_D^{20}$=1.5020; NMR, (CDCl$_3$: 0.9 (6H, s, C(CH$_3$)2), 1.05 (3H, s, CH$_3$—C). 1.2–2.0 (8H, m), 2.2–2.6 (2H, m, COCH$_2$). 3.0–3.45 (2H, m, CH$_2$N) , 2.55–2.75 (3H, m, CH2OH), 4.1 +4.45 (1H, m, N—CH anti+syn).

from tetrahydro-1,2,3,4-isoquinoline, the derivative:

1,2,3,4-tetrahydro-2(γ-hydroxybutyryl)isoquinoline (FCE 27407); yield 72.5%, $n_D^{20}$=1.5681; NMR, (CDCl$_3$): 1.92 (2H, m, COCH$_2$CH$_2$), 2.55 (2H, m, COCH$_2$CH$_2$), 2.88 (2H, m, N-CH$_2$—CH$_2$—arom.), 3.2 (1H, b.s., .OH), 3.70 (2H, m, N—CH$_2$— CH$_2$—arom.), 3.82 (2H, t, CH$_2$OH), 4.66 (2H, d, N—CH$_2$—arom.), 7.1 (4H, m, arom.).

Example 2

Compounds with A=CH=CH (trans)

6-(γ-hydroxycrotonyl)-1,3,3-trimethyl-6-azabicyclo(3,2,1)octane (FCE 27363).

A solution of 4.17 ml (0.0437 mol) of ethyl chloroformate in 50 ml of diglyme is added, in the course of 45 minutes, to the solution, which has been cooled to 0° C., of 11 g (0.0437 mol) of trans-β-(N-1,2,3-trimethyl-6-azabicyclo[3,2,1]octane) carboxamide] acrylic acid and 6 g (0.06 mol) of triethylamine in 250 ml of diglyme. After agitation at 0° C. for 2 hours, 3.2 g of sodium borohydride are added in 1 hour, maintaining the temperature at 0° C. After 90 minutes at this temperature, 250 ml of cold water are added, maintaining the temperature between 0° and 5° C.; the agitation is continued at 15° C. for 16 hours. The solution is concentrated under vacuum and, after addition of 60 ml of water, the aqueous solution is extracted four times with methylene chloride. After drying and evaporation under vacuum, the residue is purified by flash chromatography over silica with a 90:10 mixture of ethyl acetate and methanol as eluant.

3.85 g (37%) of (γ-hydroxycrotonyl)-1,2,3-trimethyl-6-azabicyclo[3,2,1]octane is obtained; melting point 72°–75° C.

Trans-β-[N-(1,2,3-trimethyl-6-azabicyclo[3,2,1]octane)- carboxamide]acrylic acid.

The solution of 36 g (0.129 mol) of ethyl ester of trans-β-[(1,2,3-trimethyl-6-azabicyclo[3,2,1]octane) carboxamide acrylic acid in 390 ml of ½ N caustic potash in methanol is agitated for 3 hours at room temperature. The solution is evaporated to dryness and then acidified cold, after addition of water, with a cold solution of 1N HCl. After extraction with ethyl acetate, the organic phase is washed with water, dried, then evaporated to dryness. After trituration of the residue in the presence of isopropanol and filtration, there are obtained 24 g (yield 74%) of trans-β-[N-(1,2,3-trimethyl-6-azabicyclo[3,2,1]octane)carboxamide]acrylic acid; melting point: 161°–163° C.

Ethyl ester of trans-β-[N-(1,2,3-trimethyl-6-azabicyclo[3,2,1]octane)carboxamide] acrylic acid.

To the solution of 26.2 ml (0.154 mol) of 1,2,3-trimethyl-6-azabicyclo[3,2,1]octane and 22.4 ml of triethylamine (0.16 mol) in 250 ml of methylene chloride cooled to 5°–10° C., the solution of 25 g (0,154 mol) of chloride of trans-β-carbethoxyacrylic acid in 70 ml of methylene chloride is added in 1 hour, maintaining the temperature between 5° and 10° C. At the end of the addition, the solution is agitated at room temperature for 90 minutes, washed with water, dried, and evaporated to dryness. The residue is purified by flash chromatography over silica using a 1:1 ethyl acetate/hexane mixture as eluant. There are obtained 38.5 g (89%) of ethyl ester of trans-β-(N-[(1,2,3-trimethyl-6-azabicyclo[3,2,1]octane)carboxamide]acrylic acid; melting point 32°–38° C.

The compounds of the invention all have a psychotropic action; in particular, mnemotonic, antiparkinsonian, antidepressive and antipsychotic activities.

DESCRIPTION OF THE DRAWINGS

FIG. 5A shows the content of 5-HT and 5-HIAA in mouse brain striatum in mice sacrificed 30, 60 and 120 minutes after administration of FCE 26858 at 0.25 mmole/kg i.p.;

FIG. 6 shows the decrease in rectal temperature in mice after administration of FCE 26858 at 0.25 mmole/kg i.p.;

Figure 1:
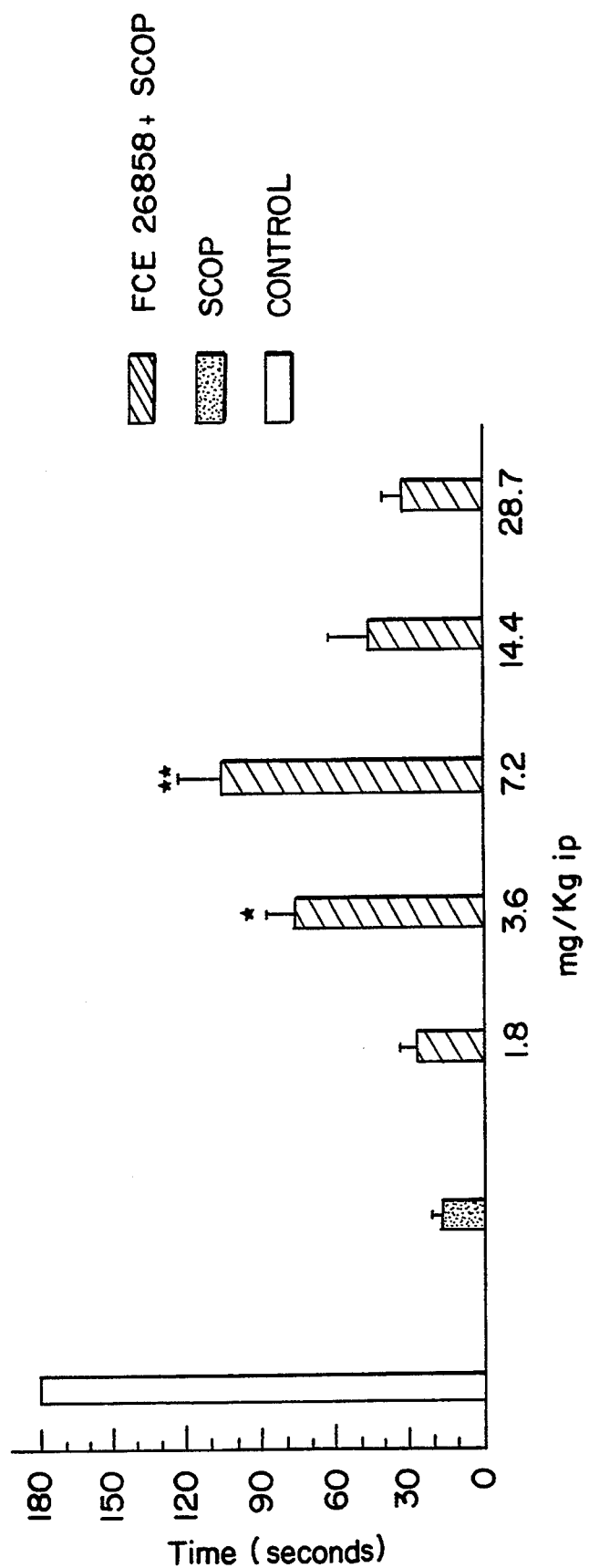
FIG. 1 shows the latency time to enter the black compartment for animals receiving scopolamine or scopolamine and FCE 26858.

By way of example, the results of experimental studies carried out on the compound FCE 26858 are indicated below:

1. MNEMOTONIC ACTIVITY

The mnemotonic activity was shown by the test of the antagonism to amnesia induced by scopolamine on a passive avoidance and an active avoidance, the "wall jump test" in mice. These activities were compared with those of ANIRACETAM, a molecule active in this type of test (Moos, W. H., et al.: Medicinal Research Reviews 8(3):353–391, 1988).

PASSIVE AVOIDANCE

Experimental Protocol

Animals

The animals used are male OF1 mice of an average weight of 30 grams, divided into lots of nine animals.

Passive Avoidance Apparatus

The training and the passive avoidance test were carried out with two black and white plexiglas cages. The white compartment (40 cm in length) is illuminated by a 100-watt bulb; the black compartment (30 cm in length) has an electrified floor formed of bars of 2 mm diameter, spaced 1 cm apart. A constant current of 1 mA is delivered (APELEX) into the bars of the black compartment. An opening of 7×7 cm in the wall separating the two halves of the cage can be closed by a sliding guillotine door.

Training and Test Method

The mice are divided at random into lots of nine animals and subjected to a training series on day 1 and tested for acquisition of the passive avoidance 24 hours later. On the training day, the mice are placed individually into the illuminated white compartment, facing the black compartment.

When the mouse has entered the black compartment, the door is closed and an electric shock is administered for five seconds. Twenty-four hours later, each mouse is again placed in the white compartment facing the black compartment.

The latency time for penetrating into the black compartment is measured for three minutes. A latency time of 180 seconds is attributed to mice which do not enter the black compartment.

Drugs

The control group receives 0.9% NaCl i.p. in a volume of 0.1 ml/10 g, 20 minutes before the training.

The scopolamine group receives 0.9% NaCl 15 minutes before the i.p. injection of scopolamine hydrobromide 0.3 mg/kg administered 5 minutes before the training.

The FCE 26858 is administered 15 minutes before the scopolamine in doses of 0.0075, 0.015. 0.030, 0.060 and 0.12 mmol/kg (1.8, 3.6, 7.2, 14.4 and 28.7 mg/kg i.p.).

The ANIRACETAM is administered 15 minutes before the scopolamine in doses of 0.23, 0.32, 0.45, 0.63 and 0.88 mmol/kg (50, 70, 98, 137.2 and 192.1 mg/kg i.p.).

Results

Figure 2:
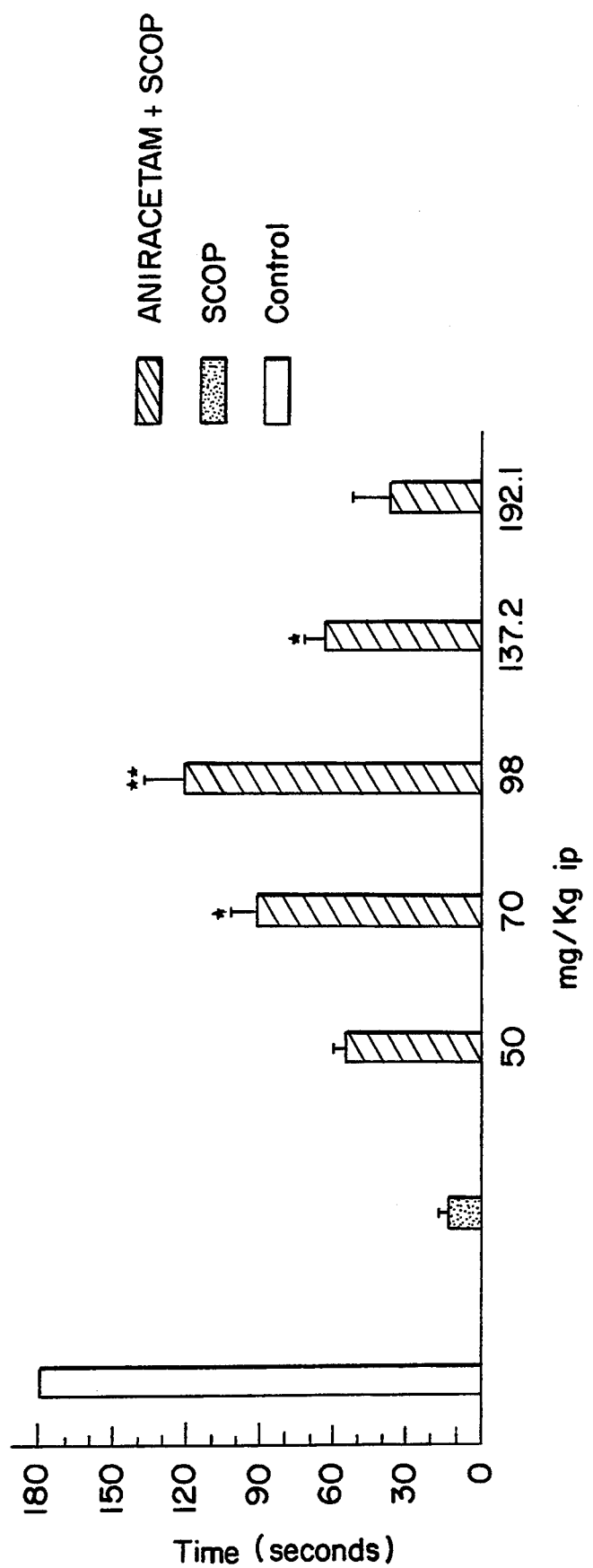
FIG. 2 shows the latency time to enter the black compartment for animals receiving scopolamine or scopolamine and Aniracetamn.

The results are set forth in FIGS. 1 and 2. The latency times are compared by means of the Mann and Whitney U test with * for $p<0.05$ and ** for $p<0.01$.

In order to compare the two molecules, we calculated an $ED_{50}$ corresponding to the effective dose which completely antagonizes the amnesia induced by the scopolamine in 50% of the animals.

FIGS. 1 and 2 show that 0.3 mg/kg of scopolamine i.p. decreases the latency time for penetration into the black compartment 24 hours after training and that the FCE 26858 and the ANIRACETAM significantly oppose this amnesia as a function of the doses. The inverted U curve of the results is conventional for active products in this type of test.

The calculation of the $ED_{50}$ gives us:

for FCE 26858: 7.6 mg/kg i.p. [3.8–1.53] 0.032 mmol/kg i.p.

for ANIRACETAM: 78.3 mg/kg i.p. [59.8–102.4] 0.36 mmol/kg, i.p.

namely a ten times greater activity for FCE 26858 than for ANIRACETAM.

STUDY OF FCE 26858 AND ANIRACETAM ON AN ACTIVE AVOIDANCE TEST: "WALL JUMP TEST"

Experimental Protocol

Animals

The experiment was carried out on male mice of an average weight of 30 g coming from IFFA CREDO (France). The animals are left in the laboratory for one week under standard conditions before any experimentation.

Equipment

The equipment used is a black plexiglas box (40×35×30) having a floor formed of electrifiable bars of 2 mm in diameter, spaced 1 cm apart. A current of 0.35 mA is administered (24 V power supply, Campden Instrument, Ltd.). The compartment can be illuminated by a 100-watt bulb. The three walls of the box are covered with a plasticized netting permitting the animals to hand thereon.

Procedure

On day 1, the animal is placed in the box for 30 seconds to permit exploration; at $t_{30}$ the light signal is actuated and at $t_{35}$ the electric shock is given. The test is interrupted when the animal jumps over one of the netting walls with a maximum shock of twenty seconds.

The second test is identical except that the exploration time is eliminated. Ten tests are carried out on days 1, 2, 3 and 8.

The average time required for the animal to jump over one of the netting walls and the average avoidance number characterized by jumping over one of the grating walls before the electric shock is noted in the ten tests. An animal which jumps over a wall before the electric shock is assigned a score of zero and an animal which does not jump over it for the entire duration of the test (5 minutes light stimulus +20 seconds electric shock) is assigned a score of twenty-five.

Drugs

FCE 26858 0.10 and 0.25 mmol/kg i.p. (24 and 60 mg/kg) and ANIRACETAM 0.46 mmol/kg i.p. (100 mg/kg) are administered 30 minutes before the test on days 1, 2, 3 and 8. The control group receives 0.9% NaCl i.p.

Results

The statistical comparison is effected by means of the Student test with * $p<0.05$ and ** $p<0.01$.

Figure 3:
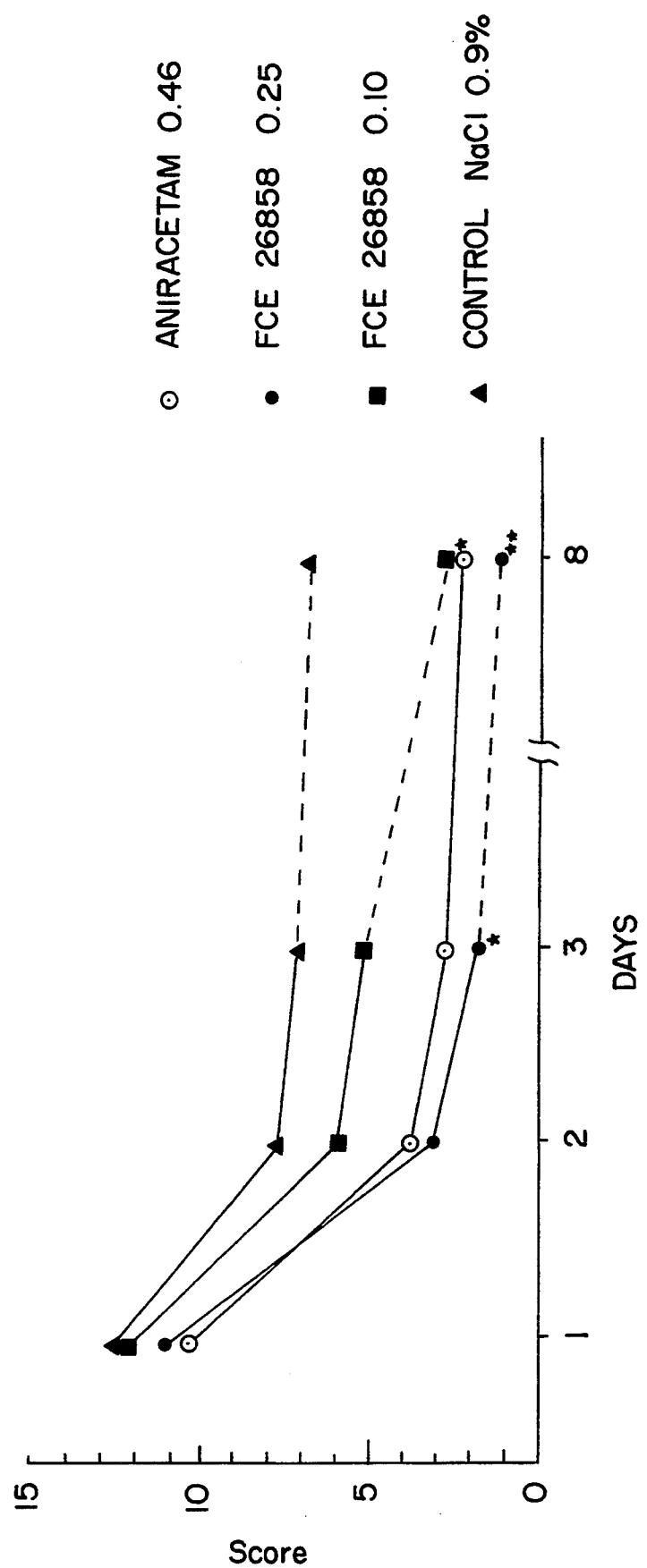
FIGS. 3 and 4 show the results obtained from a wall jump test for animals receiving FCE 26858 or Aniracetam.
Figure 4:
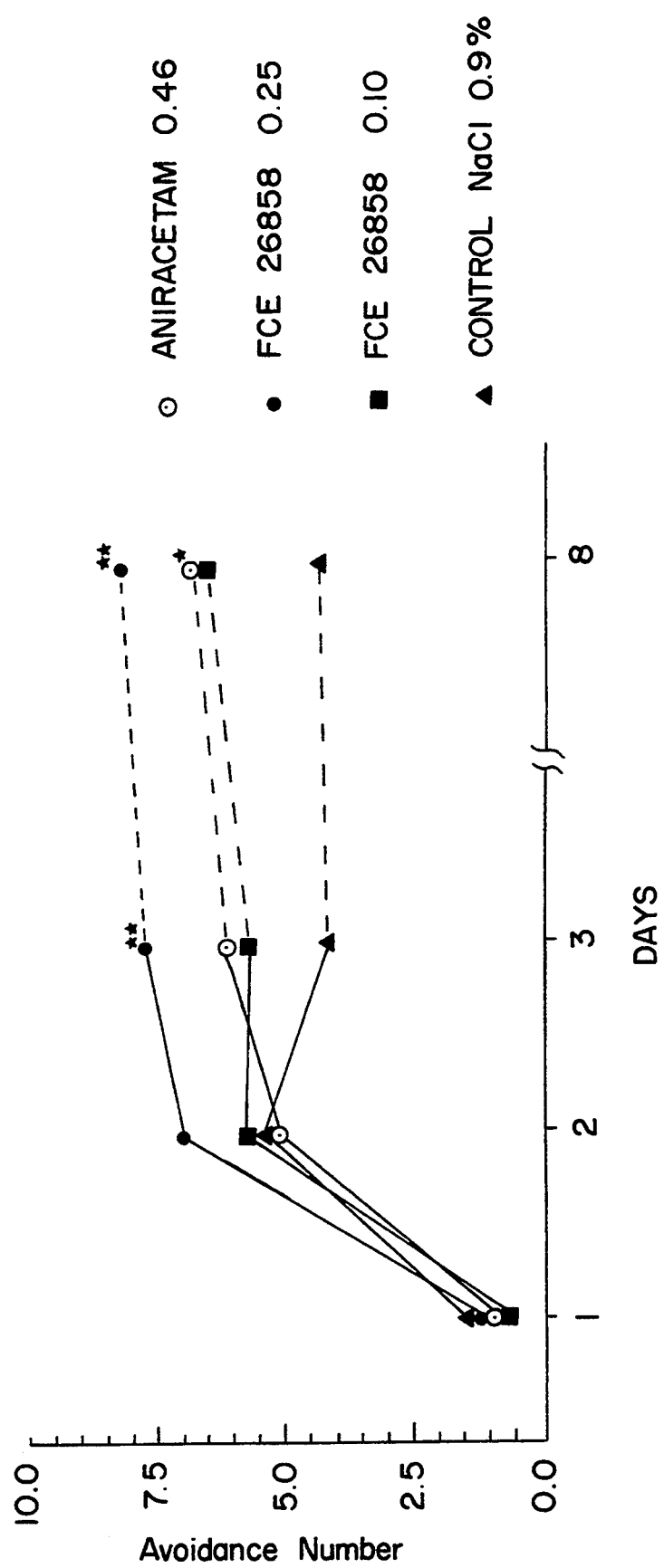

FIGS. 3 and 4 show that FCE 26858 in a dose of 0.25 mmol/kg i.p. significantly improves the two parameters of the "wall jump test" measured on days 3 and 8. ANIRACETAM, in the dose used, significantly improves these parameters only on day 8.

Conclusion

FCE 26858 therefore has an interesting mnemotonic activity which is superior to that of ANIRACETAM. Its use will be indicated in mnemic disturbances accompanying aging, cranial traumas and neurodegenerative diseases, including Alzheimer's disease.

2. ANTIPARKINSONIAN ACTIVITY

Parkinson's disease is characterized by a deficiency of the dopaminergic component of the basal ganglia, attributed to a loss of neurons in the substantia nigra. The dopamine (DA) deficit causes tremors, bradykinesia and muscular rigidity. Thus, the theoretical purpose of the treatment of Parkinson's disease is to reestablish the striatal activity by reducing the cholinergic activity or by increasing the dopaminergic function (The Pharmacological Basis of Therapeutics, Goodman and Gilman, 7th Ed., MacMillan, 1985).

Now, the administration of FCE 26858 produces in dose-dependent fashion a substantial increase in the liberation of DA in the mouse brain striatum, characterized by a high concentration of homovanillic acid (HVA) without modification of the content of DA, permitting the assumption that the synthesis of this neuromediator is retained. Furthermore, FCE 26858 never causes sterotypy.

In order to illustrate the activity of FCE 26858 on the dopaminergic system, we report below its action in a dose of 0.25 mmol/kg (60 mg/kg) upon intraperitoneal (i.p.) injection on dopamine and its metabolites of the mouse brain striatum as a function of time.

STUDY OF FCE 26858 ON THE TURNOVER OF DOPAMINE

Experimental Protocol

Animals

The animals used are OF1 male mice of an average weight of 30 grams, subjected to the standard laboratory conditions. These animals are divided into lots of seven animals each:

the control lots, receiving received an intraperitoneal injection of physiological saline solution, the test lots, receiving 0.25 mmol/kg of FCE 26858 i.p. (60 mg/kg).

The animals are sacrificed by decapitation 30, 60 and 120 minutes after administration of the products.

Dosaging Technique

The brains are rapidly removed and dissected on ice by the method of Glowinsky and Iversen. The striatums are then kept at $-70°$ C. until analysis. The samples are weighed and then homogenized with an Ultra-Turrax in 450 $\mu$l of 0.4N perchloric acid containing 0.1% EDTA and $Na_2S_2O_5$. The homogenates are centrifuged at 8000 rpm at 4° C. for 10 minutes. The supernatant is then brought to a pH of 5 by the addition of 50 $\mu$l of 10M potassium acetate. The samples are centrifuged again in the same manner as previously. The supernatant is then injected directly in the HPLC in accordance with the technique of Morier and Rips.

The HPLC system used is formed on a Waters 6000 A pump, an automatic injector cooled to 4° C. CMA 200 Carnegie Medecine, a radical compression system, a Radial Pak A column ($C_{18}$ 0.8 cm i.d.x. 10 cm, 10 $\mu$m) and a Metrohm 641 electrochemical detector. The voltage used is +0.8 V. The column is thermostatted at 30° C. and the rate of elution is 1 ml/min.

The mobile phase is formed of 0.1M $KH_2PO_4$, 0.1M EDTA, 5 mmol heptane sulfonic acid (Waters Pic B7) and 15% methanol (V/V). The pH of the mobile phase is adjusted to 4.10. All the solutions are prepared with water purified by the Millipore Milli Q system. The mobile phase is then filtered through Millipore 0.45 $\mu$m filters and then degasified.

The results are compared by the Student t test as NS (not significant); * $p<0.05$;  $p<0.01$; * $p<0.001$.

Results

Figure 5:
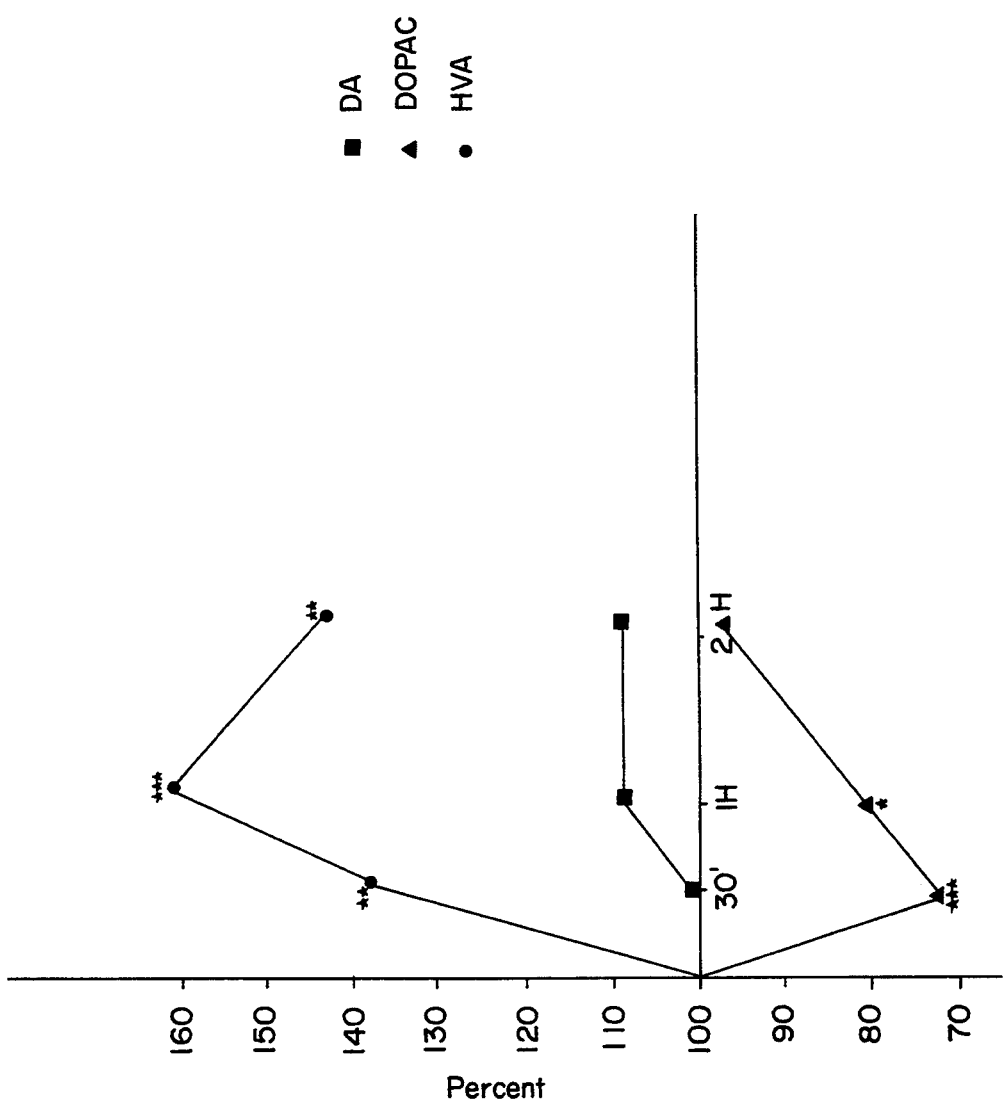
FIG. 5 shows the content of DA, DOPAC and HVA in mouse brain striatum in mice sacrificed at 30, 60 and 90 minutes after administration of FCE 26858 at 0.25 mmole/kg i.p.

FIG. 5 shows that FCE 26858 causes an increase in the HVA, a decrease in the DOPAC (3-4-dihydroxyphenylacetic acid) as a function of time. The content of DA is not significantly changed.

These results indicate an increase in the liberation of DA with preservation of the synthesis.

We also studied the action of the FCE 26858 on an animal model of the trembling characteristics of Parkinson's disease (Kaakkola, S., et al., Pharmacology and Toxicology, No. 67:95–100, 1990).

ACTION OF THE FCE 26858 ON THE Tremors AND HYPOTHERMIA INDUCED BY OXOTREMORINE 1 MG/KG I.P. IN THE MOUSE Experimental Protocol The study is carried out on male mice of an average weight of 35 grams. The FCE 26858 is studied in a dose of 0.25 mmol/kg, administered intraperitoneally at the same time as the oxotremorine. The oxotremorine in a dose of 1 mg/kg (base) is injected intraperitoneally. A lot receiving 0.9% physiological saline solution i.p. at the same time as the oxotremorine is formed.

Before the injection of oxotremorine and 30 minutes after it, the rectal temperature of the animals is taken. Thirty minutes after the injection of oxotremorine, the behavioral state is observed and rated in accordance with a scale ranging from 0 to 5 in accordance with the intensity of the symptoms.

Results

In this dose, FCE 26858 substantially antagonizes tremors, rigidity and akinesia without substantially modifying the peripheral signs induced by oxotremorine (salivation, lacrimation, diarrhea). Furthermore, the decrease in rectal temperature is significantly less than that of the control group, confirming that, in this dose, FCE 26858 opposes the central effects of oxotremorine (FIG. 6).

| AVERAGE RATING OF RIGIDITY, AKINESIA AND TREMORS | | |
|---|---|---|
| CONTROL | 4.3 ± 0.28 | |
| FCE 26858 | 2.7 ± 0.28 | −37.2%** |

Conclusion

These results suggest the use of FCE 26858 in the symptomatic treatment of Parkinson's disease.

3. ANTIDEPRESSIVE ACTIVITY

The dysfunctioning of the central dopaminergic system appears more and more important in certain depressive states (Willner, P. et al., Dopamine, depression and anti-depressant drugs, "The Mesolimbic Dopamine System: From Motivation to Action", edited by P Willner and J Scheel-Krügger, p. 387, 1991)

Thus, certain antidepressants, such as AMINEPTINE or NOMIFENSINE, act by inhibiting the recapturing of dopamine, thus favoring its synaptic action (Waldmener, P. C., J. Pharm. Pharmacol., No. 34:391–394, 1982). Now FIG. 5 shows that FCE 26858 causes a liberation of dopamine without altering its synthesis and that the decrease in DOPAC (intrasynaptosomal metabolite) gives rise to the assumption that FCE 26858 inhibits the recapture of dopamine. Thus, FCE 26858 could reestablish an altered dopaminergic function in certain depressive states.

Furthermore, the role of the serotoninergic system in certain depressive states is clearly established, and clinical studies have shown that inhibitors of the recapture of serotonin (5-HT), thus favoring its transmission, are active antidepressants (Martin, P., et al., Psychopharmacology No. 101: 406–407, 1990).

Thus, the antidepressant activity of FCE 26858 could be reinforced by its action in facilitating serotoninergic transmission since its administration causes an increase in the metabolite of 5-HT, 5-hydroxyindole acetic acid (5-HIAA), without decreasing the amount of 5-HT (FIG. 5bis).

We also tested FCE 26858 in an animal model of the depression of "behavioral despair" or forced swimming test (Porsolt, R., et al., Pharmacological models of depression, p. 137, in "Animal Models in Psychopharmacology Advances in Pharmacological Sciences", 1990).

STUDY OF FCE 26858 ON THE FORCED SWIMMING TEST

Experimental Protocol

The mice are forced to swim individually in a plexiglas cylinder (height: 26 cm; diameter: 19 cm) containing 10 cm of water maintained at 24° C.±1° C., for 6 minutes.

The animals are then dried and then warmed in an enclosure heated to 30° C. 24 hours later, the mice are placed back in the cylinder for 6 minutes and the total time of immobility is measured (the animal is considered immobile when it carries out only the movements necessary for it to float).

Administration of the Drugs

Three lots are prepared:
an 0.9% NaCl i.p. control lot;
a 25 mg/kg i.p. imipramine lot (reference molecule); and
an 0.10 mmol/kg FCE 26858 lot (24 mg/kg i.p.).

The treatments are administered one hour and five hours after the first forced swimming session and one hour before the test.

Results

Figure 7:
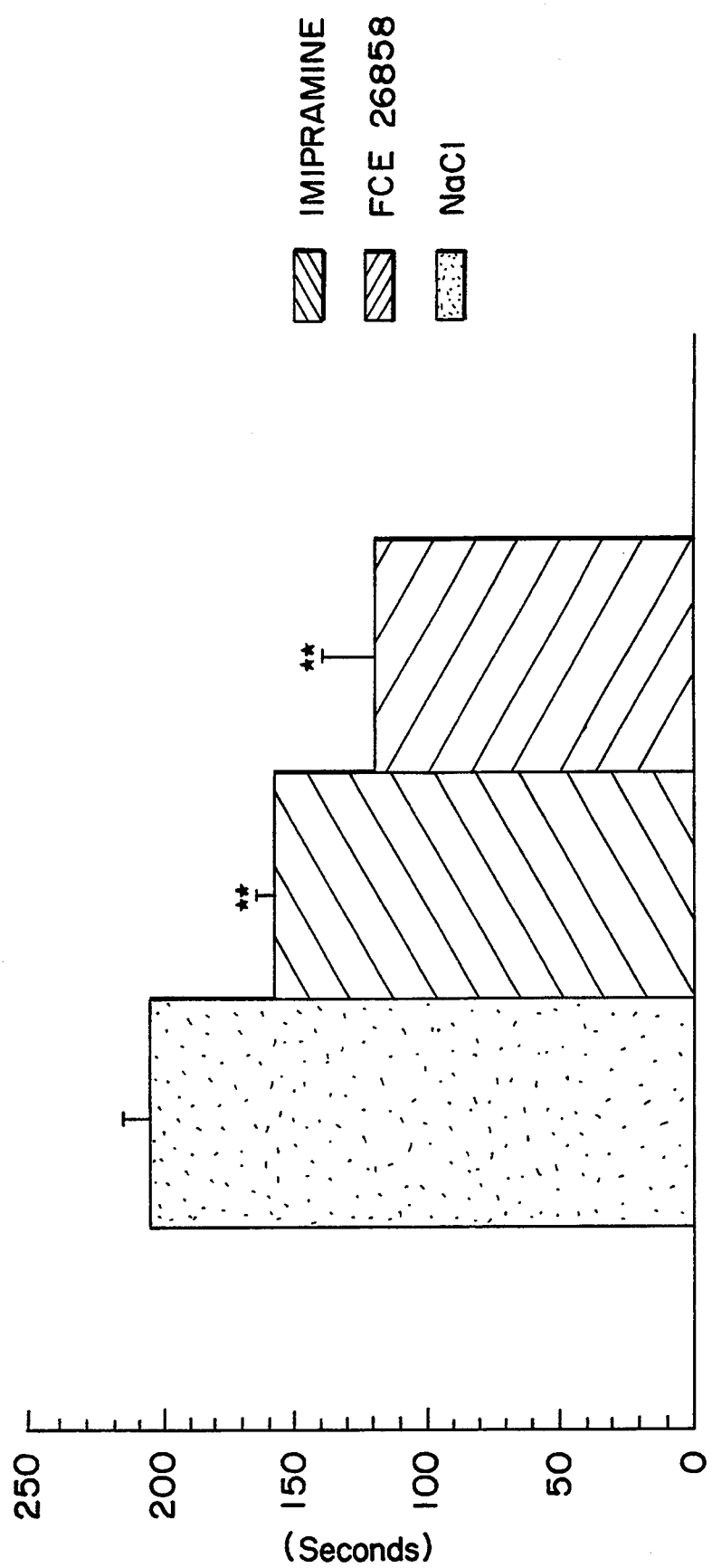
FIG. 7 shows the duration of immobility of mice in the forced swimming test after administration of 25 mg/kg i.p. of Imipramine, 24 mg/kg i.p. of FCE 26858 and 0.9% sodium chloride as control.

FIG. 7 shows that FCE 26858 significantly decreases (Student's test ** $p<0.01$) the period of immobility, like imipramine.

Conclusion

The results of FCE 26858 on the turnover of DA and 5-HT and on the forced swimming test explain its use in the treatment of depressive states.

4. ANTIPSYCHOTIC ACTIVITY

We tested the action of FCE 26858 in the latent inhibition test in rats, animal model of the attention deficit of schizophrenics. The neuroleptics have a facilitating effect in this model and Feldon and Weiner (Biol. Psychiatry, No. 29: 635–646, 1991) describe the latent inhibition as a test which makes it possible to detect the antipsychotic potential of certain molecules.

STUDY OF FCE 26858 ON THE LATENT INHIBITION TEST

Experimental Protocol

Animals

The animals used are Sprague-Dawley rats of a weight of 250–300 grams, separated into groups of 7 animals each.

Apparatus

The apparatus used is a cage rocking around an axis between two identical compartments separated by an opaque partition having an escape hole.

The floor is formed of electrifiable bars of a diameter of 2 cm, spaced 1 cm apart.

The nociceptive electric discharge (1 mA), preceded by an acoustic stimulus, is programmed by an UGO BASILE automatic reflex conditioner.

The conditioning cage is placed in a soundproof enclosure.

The protocol of the latent inhibition consists of two stages: the pre-exposure (PE) and the avoidance test.

Pre-exposure:

Each animals is placed in the conditioning cage and receives 10 or 50 acoustic stimuli of 6.5 seconds each, with an interval between the stimuli of between 20 and 36 seconds.

The non-pre-exposed animals (NPE) are placed in the cage for the same time but receive no stimulus.

Avoidance Test: 24 hours after the pre-exposure, each animal is placed in the conditioning cage and receives 60 avoidance tests with an interval between the tests of from 20 to 36 seconds. Each avoidance test starts with the presentation of the acoustic stimulus for 3 seconds, followed by an electric stimulus for 3.5 seconds. The acoustic stimulus remains for the duration of the electric stimulus. If the animal passes into the opposite compartment during the first 3 seconds of the acoustic stimulus, the electric shock is not delivered and the avoidance is counted.

The 60 tests are divided into blocks of 12 tests each, and the results are expressed in percentage of avoidance in each block.

Comparison of the groups is effected by means of variance analysis with * $p<0.05$ and ** $p<0.01$.

Drugs 0.9% NaCl, 50 mg/kg sulpiride (reference neuroleptic) and 0.10 mmol/kg FCE 26858 (24 mg/kg i.p.) are administered one hour before the pre-exposure and the test.

Results

Figure 8A:
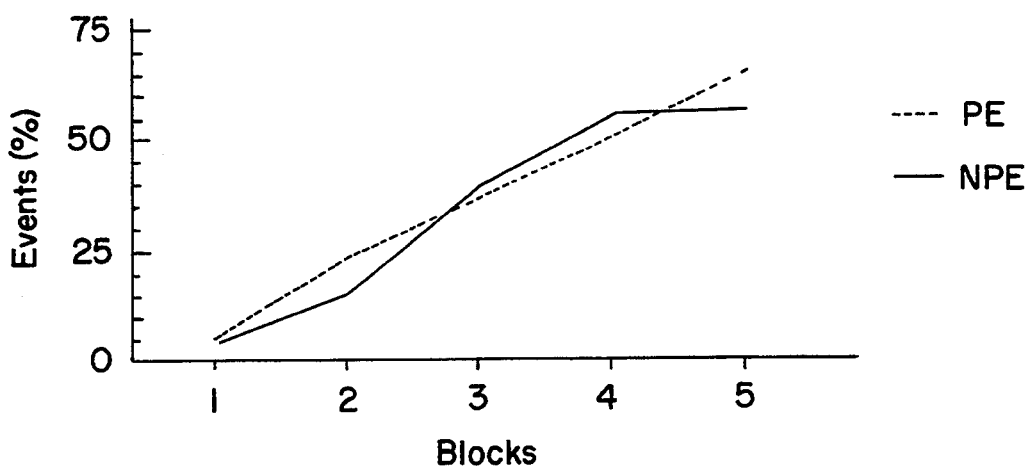
FIGS. 8A and 8B show the results of latent inhibition tests at 10 and 50 conditioning stimuli, respectively, of animals preexposed (PE) and non-preexposed (NPE) to sodium chloride.
Figure 8B:
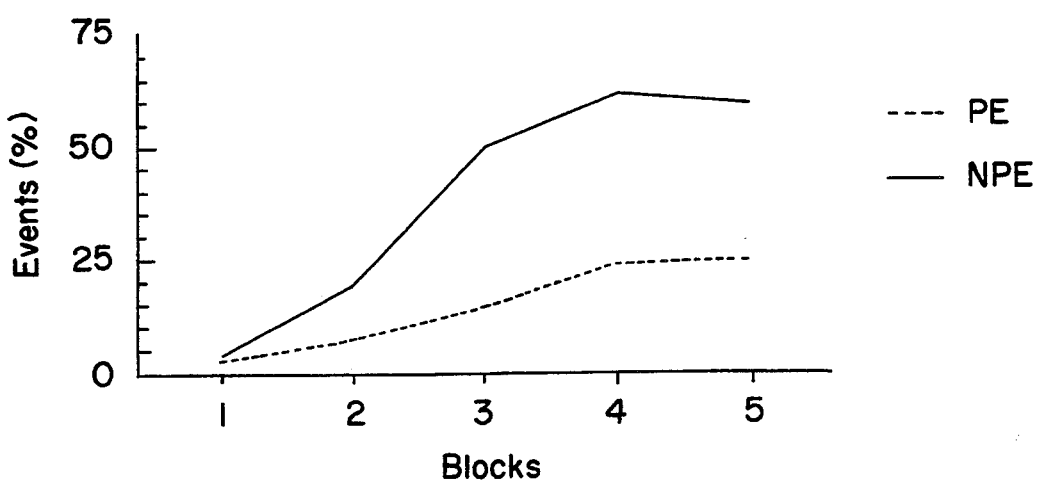

FIG. 8 shows that the pre-exposure of the animals to 50 acoustic stimuli causes a significant decrease in the PE group of the percentage of avoidance characterizing latent inhibition. On the other hand, if the number of acoustic stimuli is limited to 10 upon the pre-exposure, this is not sufficient to induce a latent inhibition 24 hours afterwards in the control group.

Figure 9:
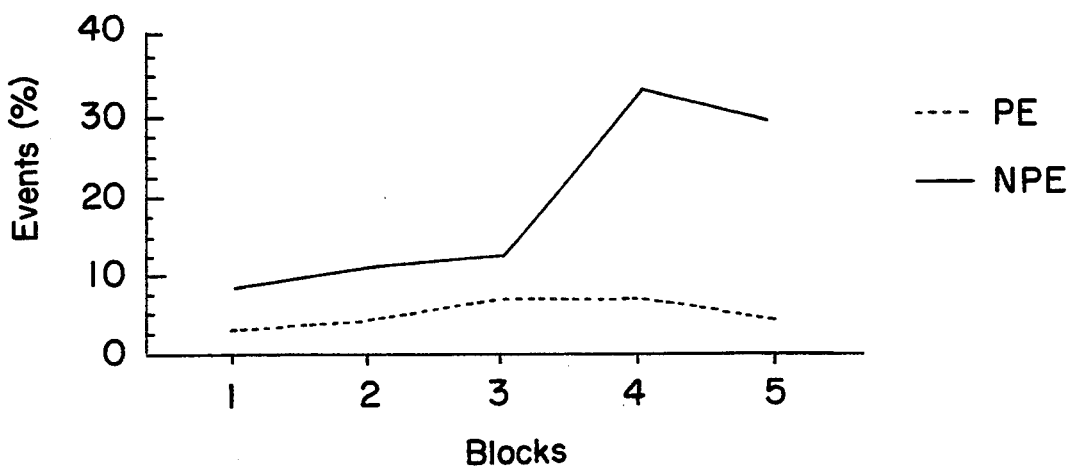
FIG. 9 shows the results of latent inhibition tests at 10 conditioning stimuli of animals preexposed (PE) and non-preexposed (NPE) to sulpuride.

However, if the animals receive 50 mg/kg sulpiride, a significant latent inhibition appears in the group preexposed with 10 stimuli only (FIG. 9).

Figure 10:
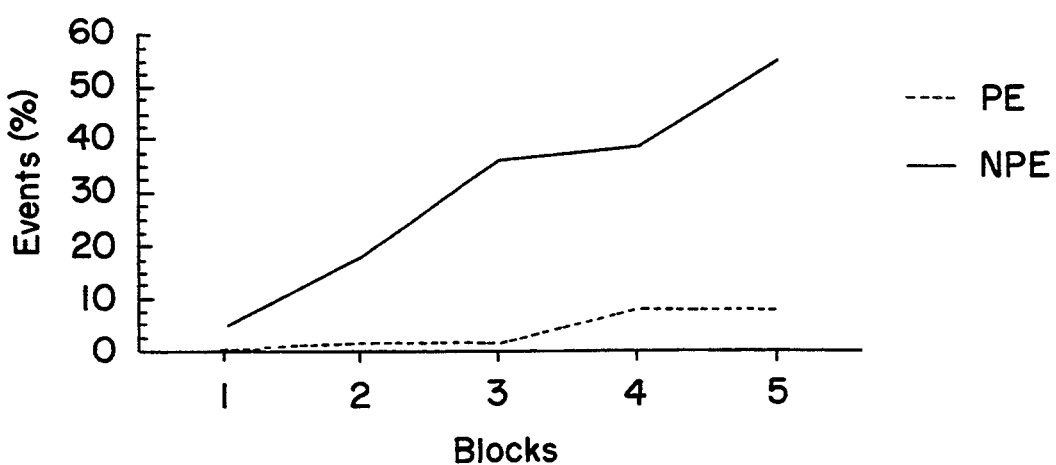
FIG. 10 shows the results of latent inhibition tests at 10 conditioning stimuli of animals preexposed (PE) and non-preexposed (NPE) to FCE 26858.

Similarly, FCE 26858 24 mg/kg i.p. favors the appearance of the latent inhibition in animals pre-exposed to 10 acoustic stimuli (FIG. 10).

Conclusion

The results show that, like sulpiride, an atypical neuroleptic, FCE 26858 favors the appearance of latent inhibition, thus explaining the antispychotic potential of this molecule.

GENERAL CONCLUSION

The experimental results presented here show that the products of the invention can be used in human therapeutics in various neurological and psychiatric ailments, namely:
treatment of mnetic disturbances associated with age, with cranial traumas, and with degenerative diseases, in small doses,
symptomatic treatment of Parkinson's disease,
treatment of depressive states,
treatment of psychoses.

These products can be administered orally or parenterally and have a very favorable therapeutic coefficient since the $LD_{50}$ of FCE 26858 is 380 mg/kg i.p. in the mouse.

The compounds of the present invention are useful in the treatment of neurological and psychiatric disorders in animals. Suitably, the compounds are administered as pharmaceutical composition comprising an effective amount of the compound in combination with an inert diluent or carrier therefor. The compounds may be administered intraperitoneally. The compounds will be administered in an amount taking into account the health and age of the patient and the severity of the disease. A suitable dosage i.p. may be from about 0.10 to about 0.25 mmole of compound (I) per kg of body weight.

TABLE 1

| | FCE |
|---|---|
| 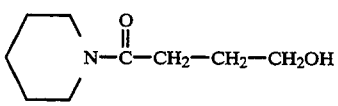 | 26099 |
| 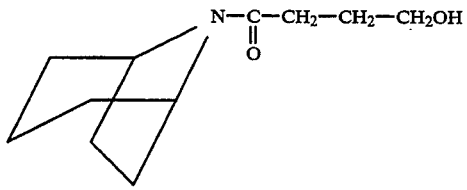 | 26630 |
| 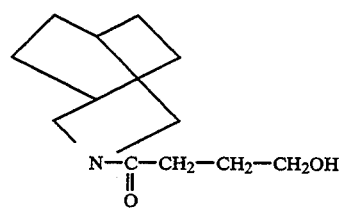 | 26857 |
| 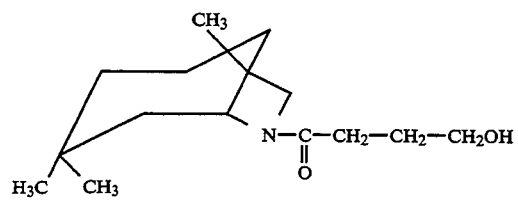 | 26858 |
| 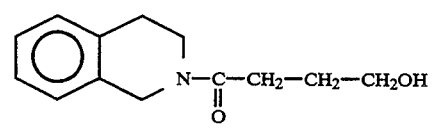 | 27407 |

TABLE 1-continued

| | FCE |
|---|---|
| 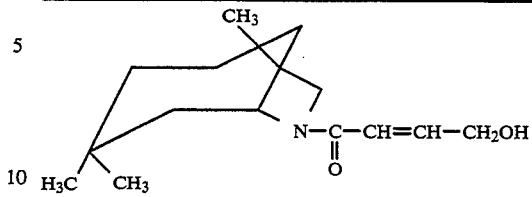 | 27363 |

We claim:

1. A compound having the general formula

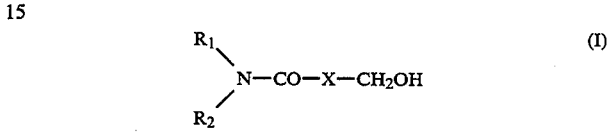 (I)

in which the cyclic system

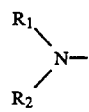

represents nor-tropane, 3-aza-bicyclo[3,2,2]nonane, 6-azabicyclo[3,2,1]octane or tetrahydro-1,2,3,4-isoquinoline, optionally substituted by up to three methyl groups, and X represents the radical $CH_2$—$CH_2$ or CH=CH (trans).

2. The compound according to claim 1, which is 6-(γ-hydroxybutyryl)-1,3,3-trimethyl-6-azabicyclo[3,2,1]octane.

3. A method for the treatment a human suffering from a neurological or psychiatric disorders, which comprises administering to the sufferer an effective amount of the compound of claim 1.

4. A method for the treatment a human suffering from a neurological or psychiatric disorders, which comprises administering to the sufferer an effective amount of the compound of claim 4.

5. A pharmaceutical composition for the treatment of a human suffering from a neurological or psychiatric disorder, comprising an effective amount of a compound of claim 1 and an inert diluent or carrier therefor.

6. A pharmaceutical composition for the treatment of a human suffering from a neurological or psychiatric disorder, comprising an effective amount of a compound of claim 2 and an inert diluent or carrier therefor.

* * * * *